United States Patent
Raheman

(10) Patent No.: US 8,303,500 B2
(45) Date of Patent: Nov. 6, 2012

(54) PRESCRIPTION ZERO: A NON-PHARMACEUTICAL PRESCRIPTION DEVICE FOR PRESCRIBING, ADMINISTERING, MONITORING, MEASURING AND MOTIVATING A THERAPEUTIC LIFESTYLE REGIMEN FOR PREVENTION AND TREATMENT OF CHRONIC DISEASES

(76) Inventor: Fazal Raheman, Dubai (AE)

( * ) Notice: Subject to any disclaimer, the term of this patent is extended or adjusted under 35 U.S.C. 154(b) by 381 days.

(21) Appl. No.: 12/545,172

(22) Filed: Aug. 21, 2009

(65) Prior Publication Data

US 2011/0046519 A1 Feb. 24, 2011

(51) Int. Cl.
- *A61B 5/00* (2006.01)
- *A61B 5/103* (2006.01)
- *A61B 5/117* (2006.01)
- *G06Q 10/00* (2012.01)
- *G06Q 40/00* (2012.01)
- *G06Q 50/00* (2012.01)

(52) U.S. Cl. ............ 600/301; 600/300; 600/595; 705/2; 705/4

(58) Field of Classification Search .................. 600/300, 600/301, 595; 705/2, 4
See application file for complete search history.

(56) References Cited

U.S. PATENT DOCUMENTS

| | | | | |
|---|---|---|---|---|
| 6,605,038 | B1 * | 8/2003 | Teller et al. | 600/300 |
| 7,261,690 | B2 * | 8/2007 | Teller et al. | 600/300 |
| 7,285,090 | B2 * | 10/2007 | Stivoric et al. | 600/300 |
| 8,157,731 | B2 * | 4/2012 | Teller et al. | 600/301 |
| 2004/0133081 | A1 * | 7/2004 | Teller et al. | 600/300 |
| 2004/0176226 | A1 | 9/2004 | Carlson | |
| 2005/0010087 | A1 * | 1/2005 | Banet et al. | 600/300 |
| 2005/0101845 | A1 | 5/2005 | Nihtila | |
| 2006/0089856 | A1 * | 4/2006 | Kadhiresan et al. | 705/2 |
| 2006/0100899 | A1 | 5/2006 | Tajima | |
| 2007/0100595 | A1 | 5/2007 | Earles et al. | |
| 2007/0135690 | A1 | 6/2007 | Nicholl | |
| 2007/0143068 | A1 | 6/2007 | Pasolini et al. | |

(Continued)

OTHER PUBLICATIONS

Abbas Meamarbashi. The Hardware of Portable and Wireless Physical Activity Recorder with Triaxial MEMS Accelerometer for Short-Term and High Intensity Physical Activities. Journal of Applied Sciences, 2009, ISSN 1812-5654.

(Continued)

*Primary Examiner* — Sean Dougherty

(57) ABSTRACT

The invention discloses a wearable/handheld personal communication device with hardware and software sensor modules that sense and analyze all caregiver prescribed/monitored user-lifestyle activities, and deploys such analysis in improving user's overall health in terms of reduced risks for all-cause morbidities/mortalities and eventually a life without drugs. Termed Rx Zero, such method may be prescribed not just for maintaining a healthy lifestyle, but for treatment of chronic diseases with intent to wean the patients to minimal or zero pharmacological intervention, or in combination with medications to improve prognosis of the disease under treatment.

The benefits of the Rx Zero method of the present invention extend not only to the individual and the community through high quality healthcare at lower cost, but payers by reducing the loss ratio on account of reduced cost of medical claims, and to the caregivers in terms of an effective tool that disseminates, implements and redefines "Primary Health Care" and "Prevention" at levels beyond the terms' currently understood scope that has transformed healthcare to sickcare.

8 Claims, 9 Drawing Sheets

Exemplary Block Diagram Illustrating Flow of Distributed Data Processing

U.S. PATENT DOCUMENTS

| | | | |
|---|---|---|---|
| 2007/0173705 A1* | 7/2007 | Teller et al. | 600/300 |
| 2007/0270665 A1* | 11/2007 | Yang et al. | 600/300 |
| 2007/0288266 A1 | 12/2007 | Sysko | |
| 2008/0146892 A1 | 6/2008 | LeBouef et al. | |
| 2008/0161654 A1* | 7/2008 | Teller et al. | 600/300 |
| 2008/0161655 A1* | 7/2008 | Teller et al. | 600/300 |
| 2008/0275309 A1* | 11/2008 | Stivoric et al. | 600/300 |
| 2008/0306763 A1 | 12/2008 | James | |
| 2009/0012433 A1 | 1/2009 | Fernstrom et al. | |
| 2009/0048538 A1 | 2/2009 | Levine et al. | |
| 2009/0118590 A1* | 5/2009 | Teller et al. | 600/300 |
| 2009/0177068 A1* | 7/2009 | Stivoric et al. | 600/365 |
| 2010/0016742 A1* | 1/2010 | James et al. | 600/509 |
| 2010/0160740 A1* | 6/2010 | Cohen et al. | 600/300 |

OTHER PUBLICATIONS

Makikawa, et al. Jogging Support System with Portable Monitoring Device and Health Manage Software. http://cmbi.bjmu.edu.cn/news/report/2004/medinfo2004/pdffiles/papers/4444Makikawa.pdf. Medinfo 2004.

Chen et al. A Brief Survey of Physical Activity Monitoring Devices. Mobile & Pervasive Computer Research, University of Florida, NIH Grant No. 5R21DA024294-02. http://www.icta.ufl.edu/projects/publications/chao08a.pdf. 2008.

* cited by examiner

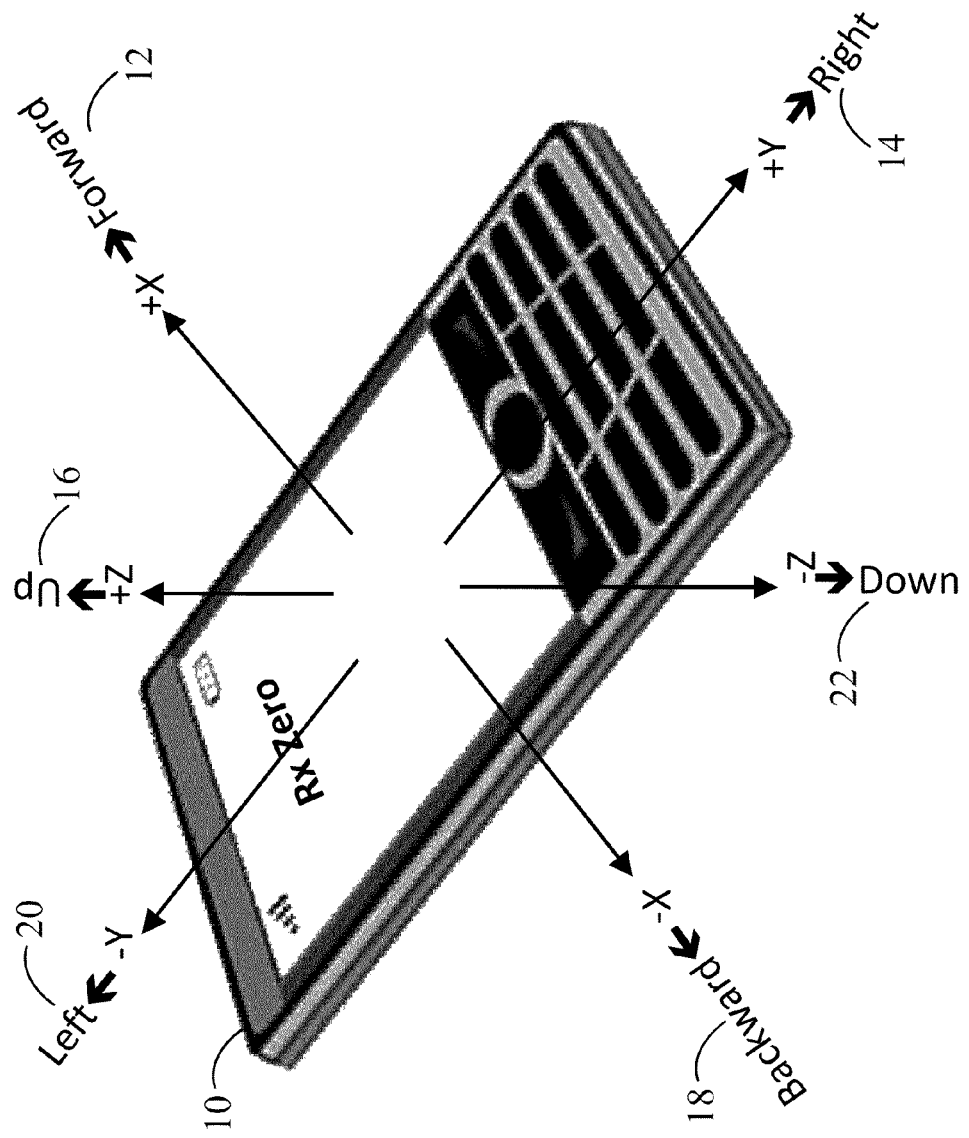
FIG 1. Orientations Showing Directions for Each Accelerometer Axis in a Composite Rx Zero Device

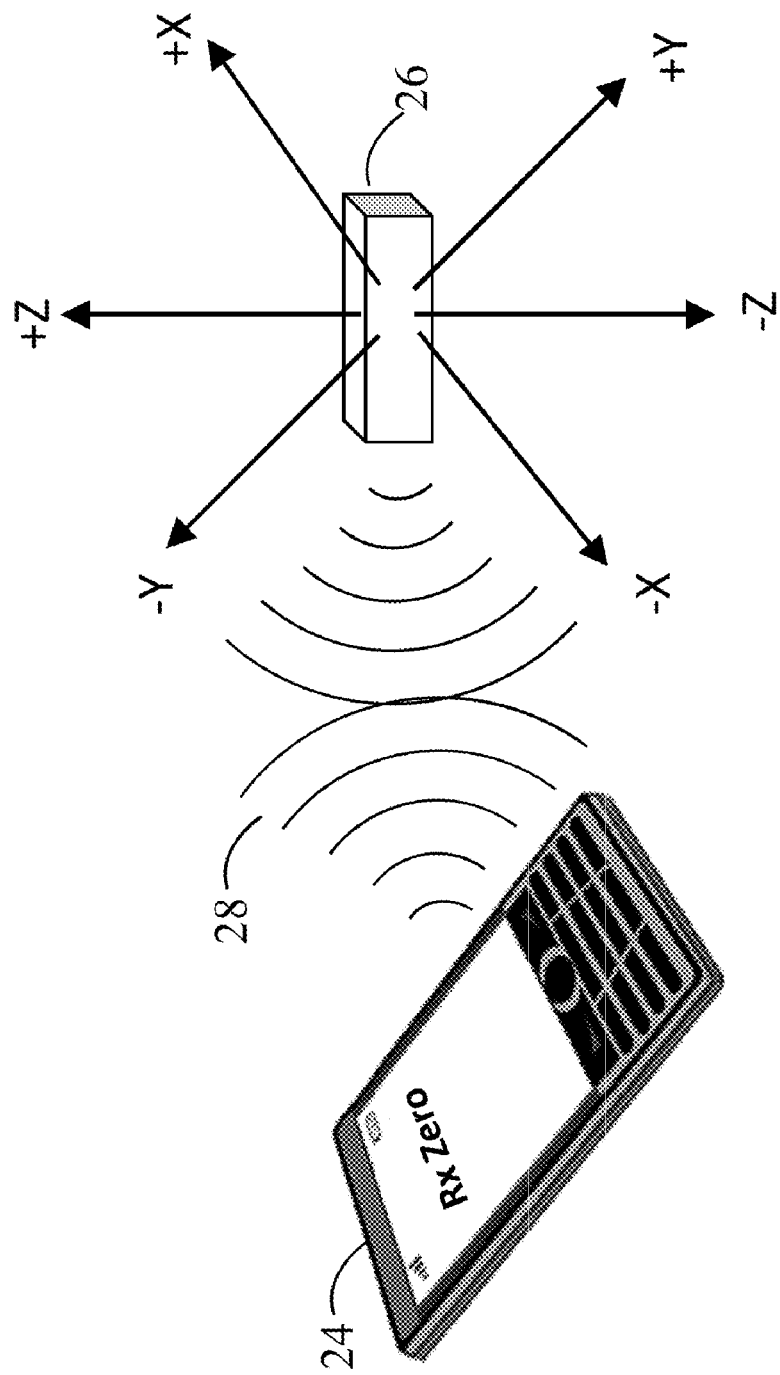
FIG 2. External Accelerometer Transmitting XYZ Axes Data to the Rx Zero Device in a Segregated Rx Zero Embodiment

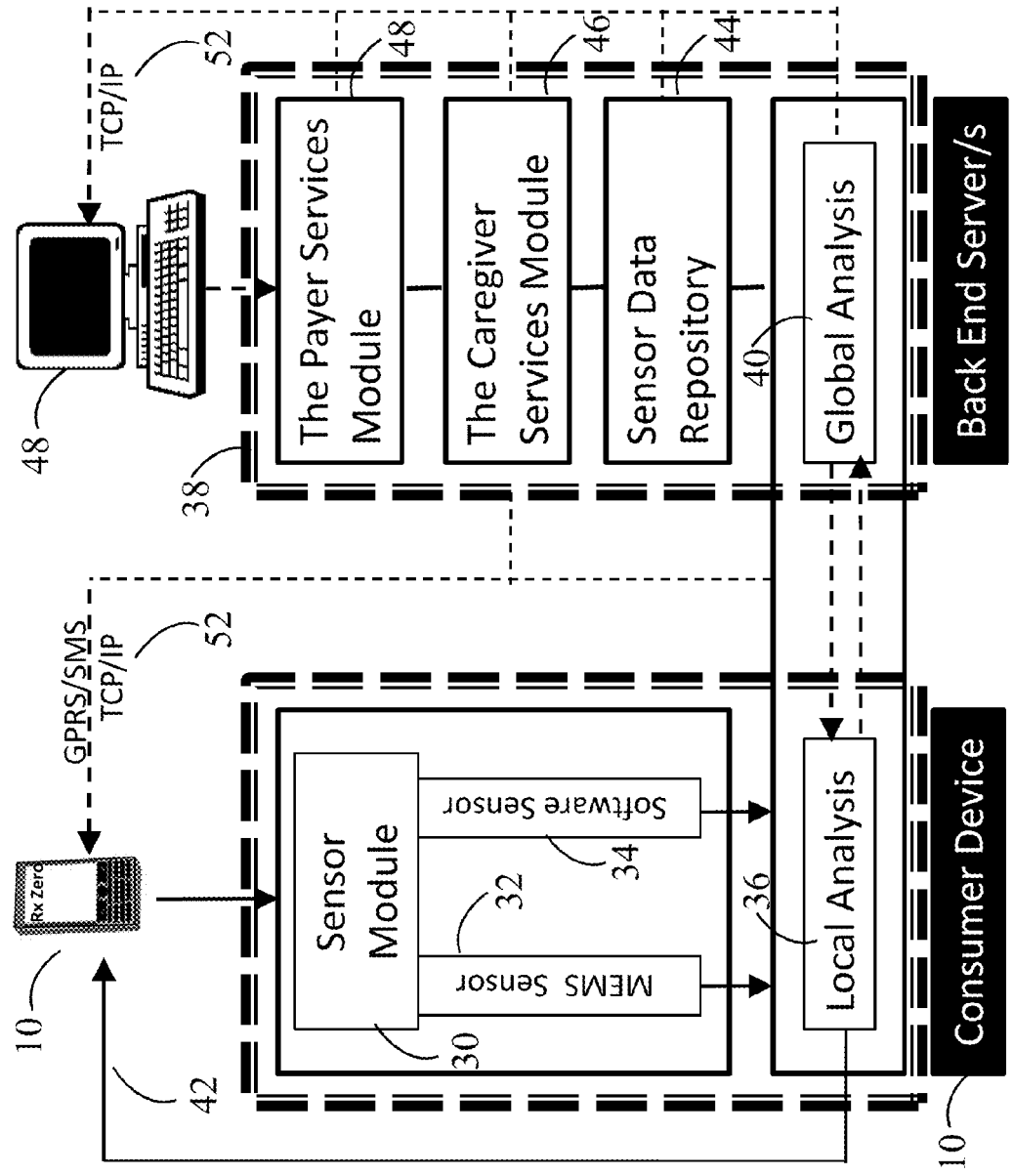
FIG 3. Network Architecture of Composite Rx Zero Device : Integrated MEMS Sensor

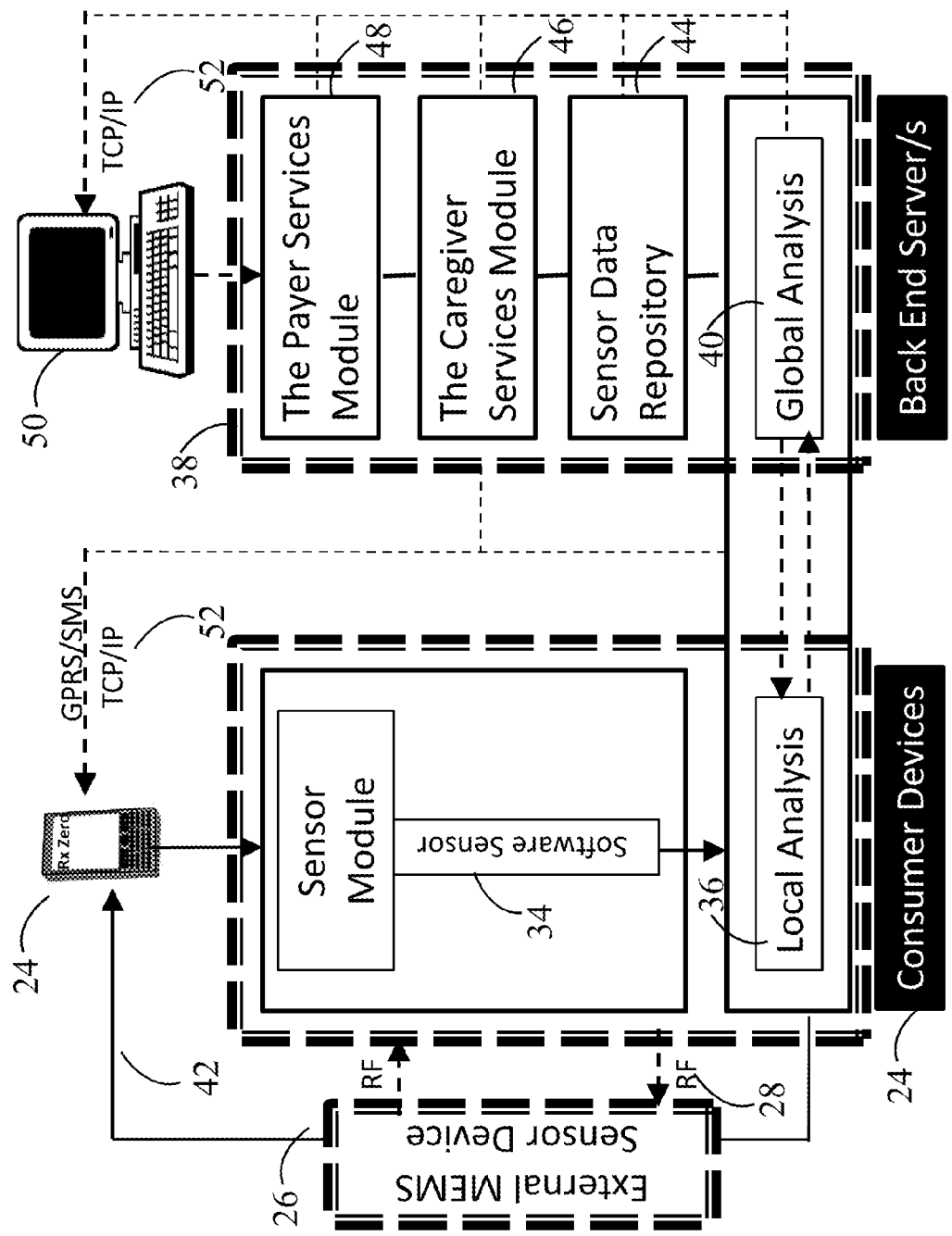
FIG 4. Network Architecture of Segregated Rx Zero Embodiment: External Accelerometer

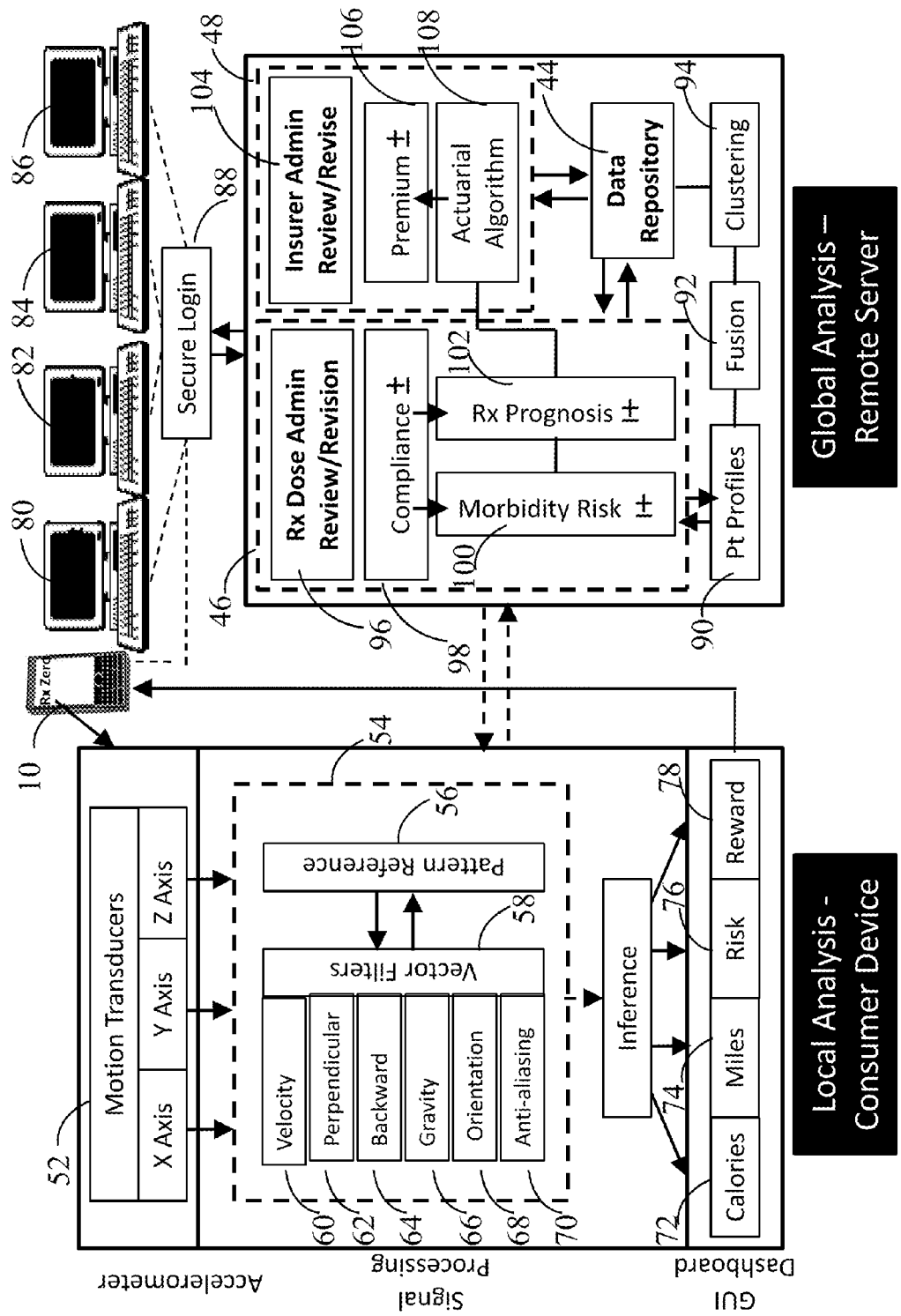
FIG 5. Exemplary Block Diagram Illustrating Flow of Distributed Data Processing

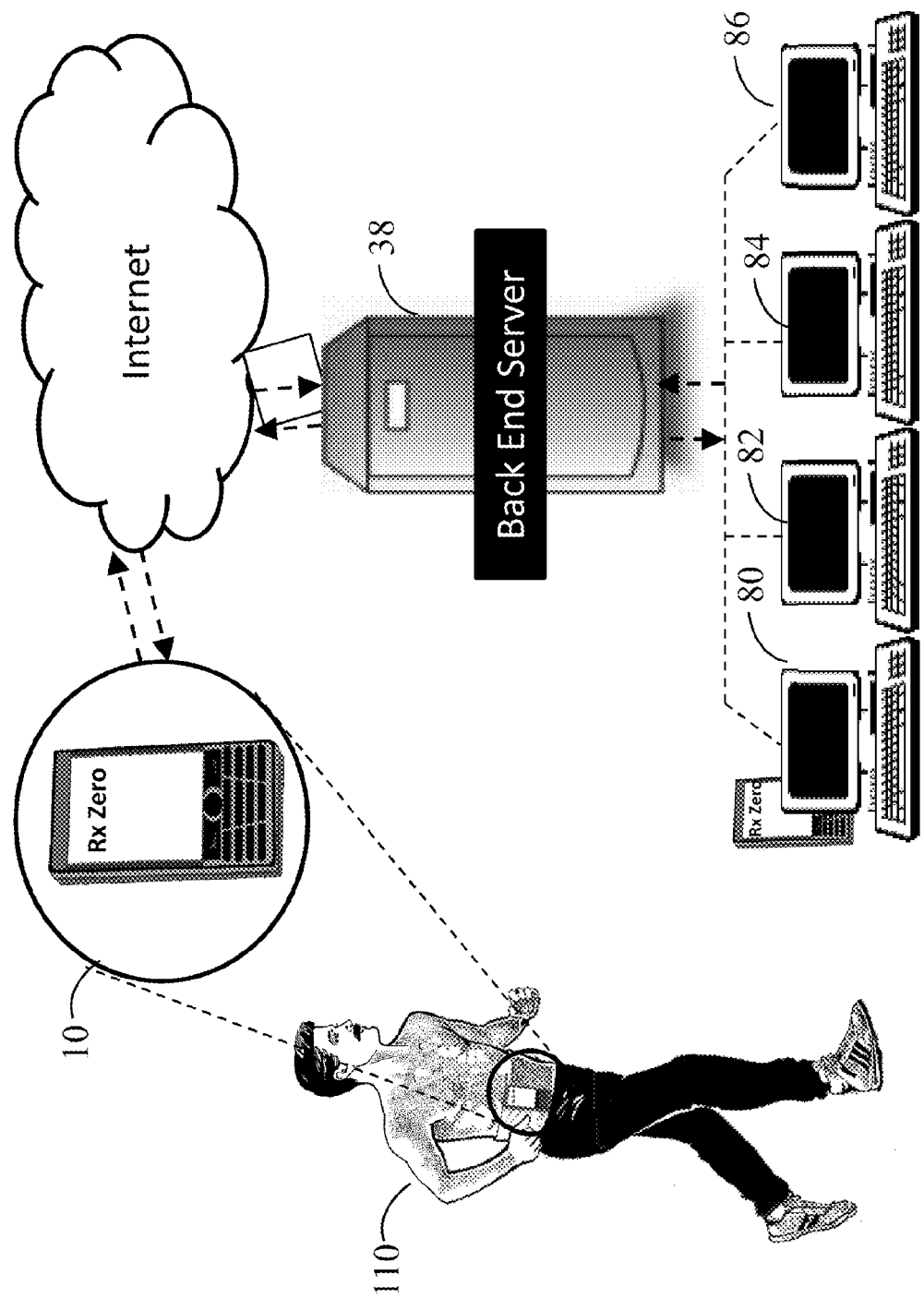
FIG 6. First Embodiment: Rx Zero Composite Device Networking

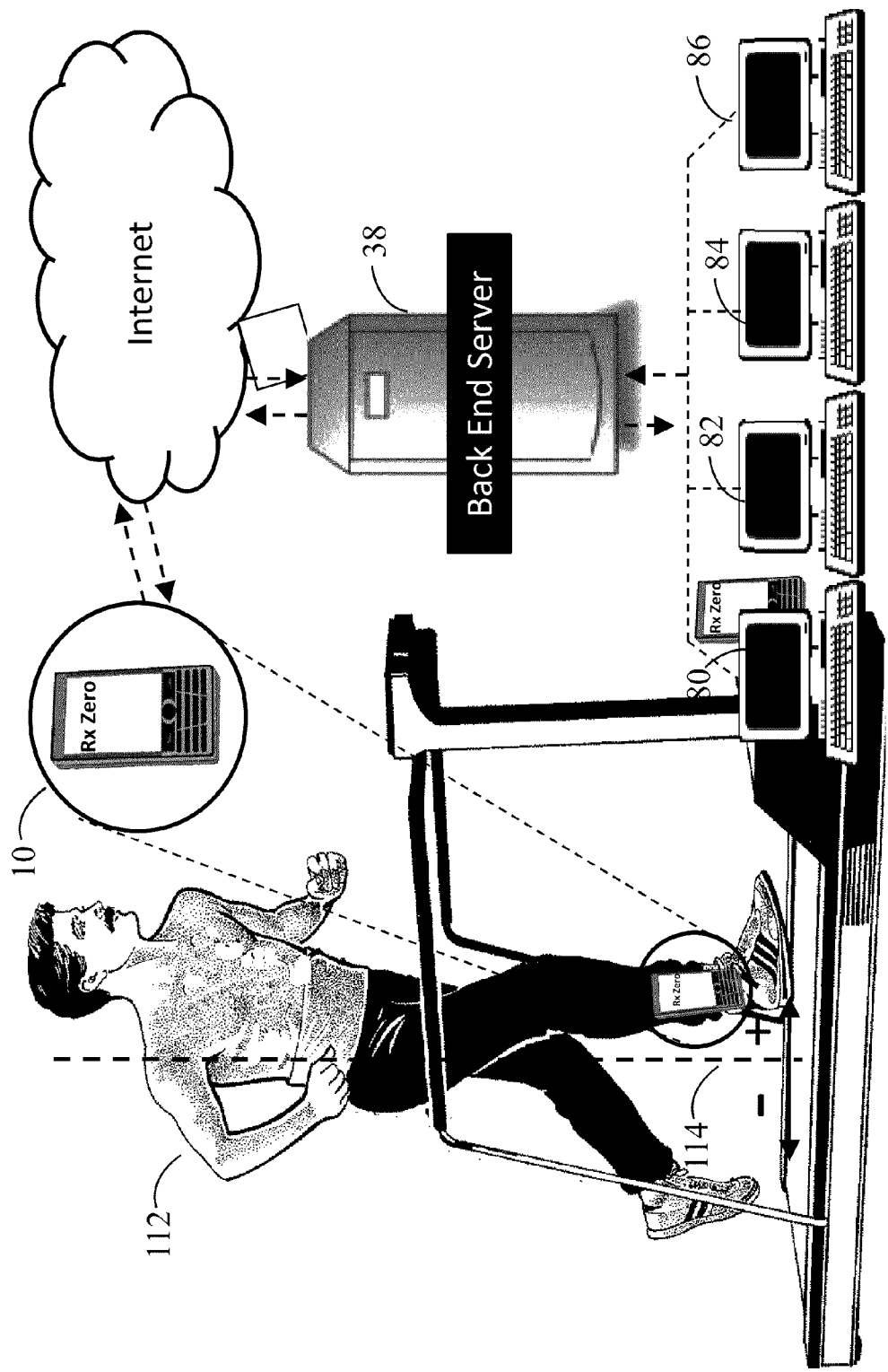
FIG 7. Second Embodiment: Rx Zero With Spatial Displacement Filtering When Used With Conventional Treadmill

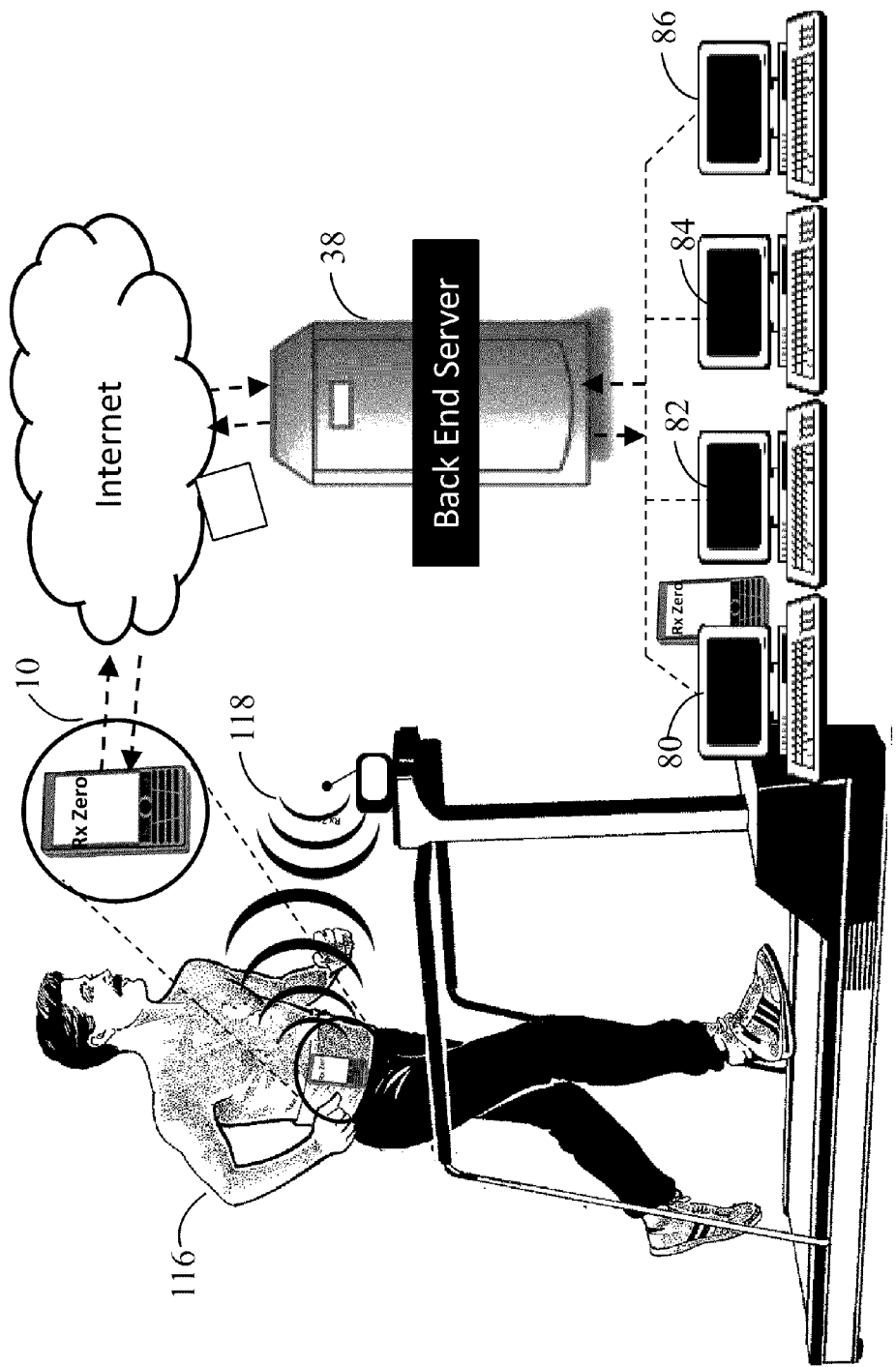
FIG 8. Third Embodiment: Rx Zero Device Networking With Treadmill's Wireless Pedometer

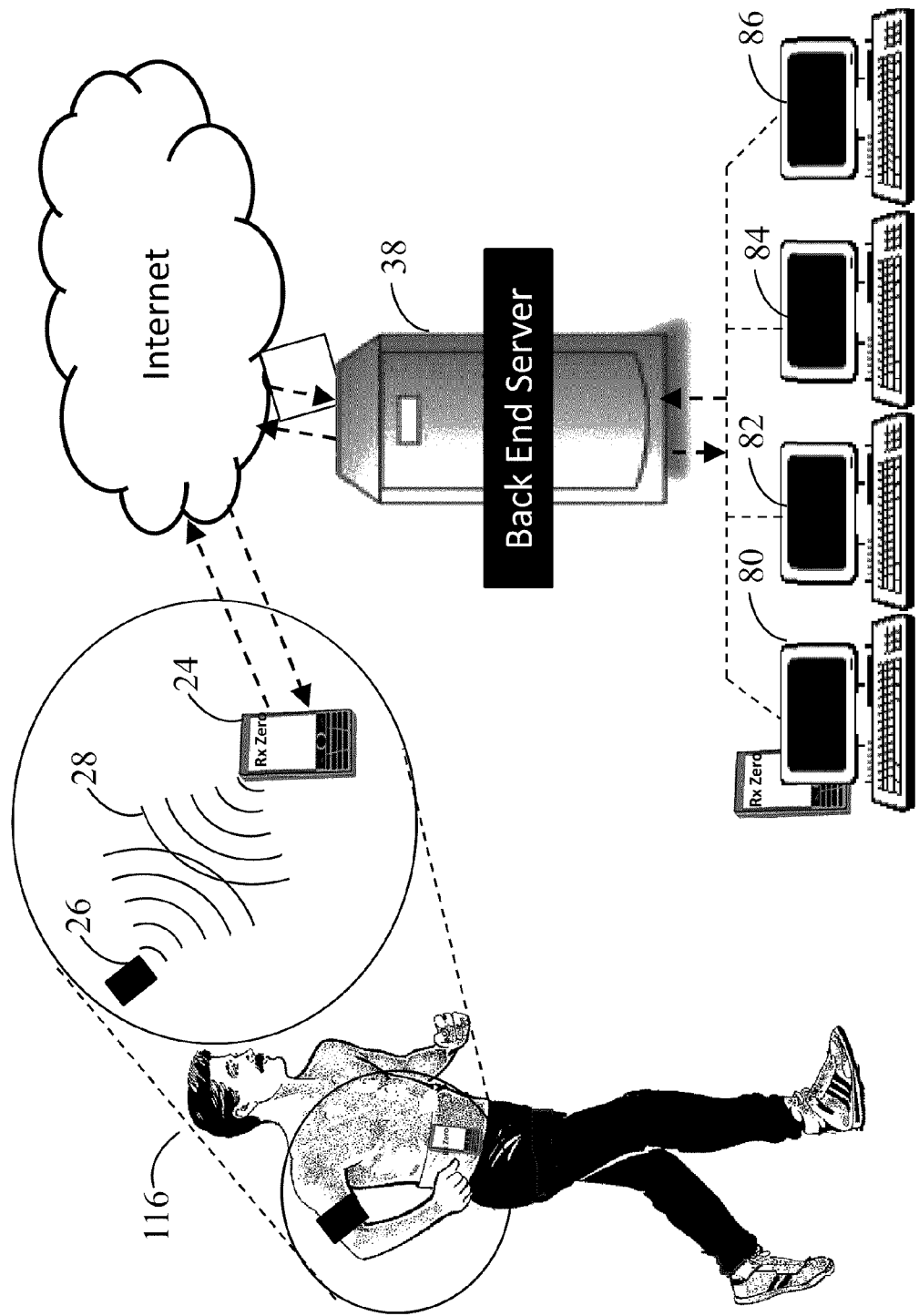
FIG 9. Fourth Embodiment: Segregated Rx Zero with External Accelerometer

PRESCRIPTION ZERO: A NON-PHARMACEUTICAL PRESCRIPTION DEVICE FOR PRESCRIBING, ADMINISTERING, MONITORING, MEASURING AND MOTIVATING A THERAPEUTIC LIFESTYLE REGIMEN FOR PREVENTION AND TREATMENT OF CHRONIC DISEASES

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention relates generally to bio-sensors particularly to wearable/handheld personal communication devices that integrate a MEMS accelerometer chip to measure and analyze user's physical activity and its impact on the user's health. More particularly the method is deployed in prescribing therapeutic exercise regimen and related lifestyle alterations to enhance quality of life and improve treatment and prognosis of several chronic diseases and consequently reduce the cost of healthcare delivery and therefore health insurance.

BACKGROUND OF THE INVENTION

Practice of western or modern medicine is based on a sickness rather than wellness paradigm. In this "sick care system," most individuals visit a doctor when they are in desperate need of medical help. One of the first criticisms of the American healthcare system as a "sick care system" came from none other than Dr Joycelyn Elders, the first African American woman appointed surgeon general by President Bill Clinton in 1993. In a recent interview she reiterated her assertion saying that, "we have the very best sick care system in the world, we just don't have a health care system." (Kay Steiger. Five Minutes With Dr Joycelyn Elders. Campus Progress, Center for American Progress, Jan. 9, 2009; www-.campusprogress.org/5mw/3538/five-minute-with-dr-joce-lyn-elders. Accessed Jun. 21, 2009). Another strong critic of the American sick care system is member of US Senate Tom Harkin. He has been campaigning to bring the real transformation of the existing sick care system, and also introduced legislation in the US legislature to that effect a couple of times.

According to the Organization for Economic Co-operation and Development (OECD), on average only 3% of total health expenditure in OECD countries goes toward population-wide prevention and public health programs, while most of the spending is focused on "sick care." Adoption of the lifestyle and culture of the Western world has resulted in 80% of chronic disease related deaths in low and middle income countries (Jacqui Wise. Research network aims to tackle chronic disease in developing world. BMJ 2009; 338:b2440). Recent years have seen enormous increase in healthcare costs and yet further decline in global health. Despite Primary Health Care (PHC) programs in place almost all of the increases are attributed to care of the sick rather than preventing the population from getting sick.

A vast proportion of resources are spent on curative services, neglecting prevention and health promotion that could cut 70% of global disease burden. Without substantially reorienting, today's struggling health systems are likely to be overwhelmed by the growing challenges of aging populations and pandemics of chronic diseases.

Since time immemorial regular exercise is regarded as an important component of disease prevention and health enhancement. Hippocrates, the father of medicine who realized the value of exercise in maintaining good health, states: "All parts of the body if used in moderation and exercised in labors to which each is accustomed, become thereby healthy and well developed, and age slowly; but if unused and left idle, they become liable to disease, defective in growth, and age quickly." The ancient Indian Yogic practices of Asanas and Pranayamas improvise health and cure chronic diseases not only by exercising the muscles, but working out the internal organs.

The increase in recent decades of life style related diseases such as obesity, diabetes and cardiovascular diseases has resulted in global pandemic that sees no decline. In the United States, approximately 65% of adults and 16% children are overweight (body mass index (BMI) at least $25 \text{ kg/m}^2$) or obese (BMI$\geq$30 $\text{kg/m}^2$). Obesity has been linked to many types of cancer (e.g., breast, colon, and prostate cancers), type 2 diabetes, coronary and congestive heart diseases, stroke, digestive diseases, respiratory diseases, osteoarthritis, and birth defects. Values of fatness and leanness are dependent on basic personal data, such as sex, age, height, weight and the like.

A large and growing body of clinical, scientific and epidemiologic evidence supports the concept of "exercise and longevity." (Elrick H. Exercise is Medicine. Phys Sportsmed 1996: 24: 72-78). Despite this overwhelming evidence, millions of adults and children remain sedentary. Based on a 1994 study it is estimated that 168,000 of the 480,000 coronary artery disease (CAD) deaths would not have occurred if everyone were optimally active. If 30% of the population were to engage in regular exercise, defined as 30 minutes of light to moderate exercise, preferably daily, approximately 24,000 deaths from CAD per year would be averted. (Powell K E. Population attributable risk of physical inactivity. Physical Activity and Cardiovascular Health. NIH Consensus Development Conference. Dec. 18-20, 1995. NIH, Bethesda, Md.)

According to the latest recommendations from the American Heart Association and the American College of Sports Medicine the evidence from the prospective studies on disease outcomes that are inversely related to regular physical activity include cardiovascular disease, thromboembolic stroke, hypertension, type 2 diabetes mellitus, osteoporosis, obesity, colon cancer, breast cancer, anxiety and depression. Scientific evidence continues to accumulate on more conclusive evidence on stroke, some cancers, and cognitive function.

AHA/ACSM advocates Class I(A) recommendation for moderate-intensity aerobic (endurance) physical activity for a minimum of 30 min on five days each week or vigorous-intensity aerobic physical activity for a minimum of 20 min on three days each week to promote and maintain health for all healthy adults aged 18 to 65 years. Furthermore, to persons who wish to further improve their personal fitness the AHA/ACSM report recommends that such individuals can further reduce their risk for chronic diseases and disabilities or prevent unhealthy weight gain by exceeding the minimum recommended amounts of physical activity, because of the dose-response relation between physical activity and health.

(Haskell W. L. et al. Physical Activity and Public Health: Updated Recommendation for Adults From the American College of Sports Medicine and the American Heart Association Circulation 2007; 116; 1081-1093).

In the HALE (Healthy Ageing: a Longitudinal study in Europe) Project Knoops et al demonstrated that lack of adherence to the low-risk lifestyle comprising of diet, nonsmoking, physical activity was associated with a population attributable risk of 60% of all deaths, 64% of deaths from coronary heart disease, 61% from cardiovascular diseases, and 60% from cancer. (Knoops T B K, et al. Mediterranean Diet, Lifestyle Factors, and 10-Year Mortality in Elderly European Men and Women. *JAMA.;* 292:1433-1439 (2004)).

More studies with larger cohorts and longer follow up keep building up a strong case for modification of lifestyle factors to improve cardiovascular health. (Forman J P, Stampfer M J, Curhan G C. Diet and lifestyle risk factors associated with incident hypertension in women. JAMA 2009; 302:401-411; Djoussé L, Driver J A, Gaziano J M. Relation between modifiable lifestyle factors and lifetime risk of heart failure. JAMA 2009; 302:394-400; and Roger, V L. Lifestyle and cardiovascular health. Individual and societal choices. JAMA 2009; 302:437-439).

Children, young adults and otherwise healthy individuals that engage in regular exercise can see their risk of acquired disease decline. Those with existing health conditions may see improvement in their disease process. Physical activity has the potential to benefit all. Even among older adults, a healthy lifestyle, one that includes physical activity, healthy dietary habits, smoking cessation, and light or moderate alcohol use, is associated with a significantly lower incidence of new-onset diabetes mellitus. Harvard researchers recently showed that 80% of new cases of diabetes are attributable to these risk factors, a number that increases when obesity is included as a risk factor. Combining low-risk groups for physical activity level, dietary habits, smoking habits and alcohol use produced an 82 percent lower risk of diabetes, and four in five new cases of diabetes appeared to be attributable to not having these low-risk lifestyle factors. Adding either not being overweight or not having large waist circumference was associated with an 89 percent lower risk of diabetes. (Mozaffarian, D. et al. Lifestyle Risk Factors and New-Onset Diabetes Mellitus in Older Adults," Archives of Internal Medicine, 2009; 169[8]:798-807).

Even cancer patients have shown better prognosis and improvement in quality of life with regular physical activity. The Health, Eating, Activity and Lifestyle (HEAL) study of 933 breast cancer patients showed that moderate-intensity physical activity reduced the risk for death by 67% in women who remained active 2 years after diagnosis. This was in both, breast cancer mortality and deaths from other causes, mostly cardiovascular disease and diabetes, (Irwin, M, et al. *J Clin Oncol.* 2008:24; 3958-3964).

In the prospective National Institutes of Health—AARP Diet and Health Study, a total of 450 416 participants aged 50 to 71 years identified 1057 eligible incident pancreatic cancer cases. Participants were scored on 5 modifiable lifestyle factors as unhealthy (0 points) or healthy (1 point) on the basis of current epidemiologic evidence. Participants received 1 point for each respective lifestyle factor: nonsmoking, limited alcohol use, adherence to the Mediterranean dietary pattern, body mass index ($\geqq 18$ and <25), or regular physical activity. A combined score (0-5 points) was calculated by summing the scores of the 5 factors. Compared with the lowest combined score (O points), the highest score (5 points) was associated with a 58% reduction in risk of developing pancreatic cancer in all participants (relative risk, 0.42; 95% confidence interval, 0.26-0.66; $P_{trend}<0.001$). (Jiao, L, et al. A Combined Healthy Lifestyle Score and Risk of Pancreatic Cancer in a Large Cohort Study. Arch Intern Med. 2009; 169(8):764-770).

A new report from UK predicts that regular exercise and healthy diet can prevent 26% of the cases of colorectal cancer. (Parkin D M, Olsen A H, & Sasieni P (2009). The potential for prevention of colorectal cancer in the UK Eur J Cancer Prev DOI: 10.1097/CEJ.0b013e32830c8d83). In yet another study Ornish et al reported that comprehensive lifestyle changes may modify the progression of prostate cancer. In a study of 30 men with low risk prostate cancer they demonstrated that the genetic profiles of the participants were changed within 3 months in response to intense lifestyle changes. (Ornish D et al. Changes in prostate gene expression in men undergoing an intensive nutrition and lifestyle intervention. PNAS Jun. 17, 2008 vol. 105 no. 24, 8369-8374). Change in lifestyle may alter genetic expression warding off pathological processes. Regular physical exercise and a heart-healthy diet, 2 of the mainstays of good physical health, may also be protective against age-related cognitive decline and dementia. (www.medscape.com/viewarticle/706680?sssdmh=dm1.506978&src=nldne)

Our bodies need to be exercised. We weren't meant to be inactive. Changing lifestyle is less expensive, and without the side-effects. Living on medications is expensive and with irreversible life-threatening side effects. In 1996 the U.S. Surgeon General (U.S. Department of Health and Human Services, 1996) endorsed public health recommendations that individuals minimally strive to accumulate 30 minutes or more of moderate intensity activity (like brisk walking) on most, if not all, days of the week. However, more than a decade later physical activity levels in population are still declining. (Weiss D. R. et al. Five-year predictors of physical activity decline among adults in low-income communities: a prospective study. Int J Behav Nutr Phys Act. 2007; 4: 2).

| Motivators and Barriers Associated with Physical Activity | |
| --- | --- |
| Motivators | Barriers |
| Feeling better/more energy | No time/too busy |
| Promote health | Exercise will not help me |
| Prevent heart attacks | Lack of confidence |
| Lower Blood Pressure | Facilities not convenient |
| Look better | Too costly |
| Lose weight | Exercise not interesting/painful |
| Personal accomplishment | Embarrassed of appearance |
| Contact with friends | Poor environment |
| Increase strength | Increased fatigue |
| Sleep better | Do not make me feel better |

Adapted from Will PM, Demko TM, George DL. Prescribing exercise for Health: A Simple Framework for Primary Care. Am Fam Physician 1996; 53: 579-585.

Some of the most important constraints cited are: lack of time, inconvenient, a belief that intervention will not be successful, lack of reward or measurable benefit, inadequate reimbursement, a lack of adequate training in physical activity and counseling. (Pate R R, Pratt M, Blair S N, Haskell W L, et al. Physical activity and public health: a recommendation from the Centers for Disease Control and Prevention and the American College of Sports Medicine. JAMA 1995; 273: 402-407).

Various approaches have been designed in prior art to combat some of these constraints by inventing various types of exercise regimen, exercise equipments, treadmills and other exercise paraphernalia. There is the issue of patient adherence, of course, with most studies suggesting that patients won't keep with a rigorous weight-loss program over the long term. Most physicians don't have training in weight-loss intervention, and "most clearly have little time for lifestyle counseling in the current medical-economic climate." Most individuals have a hard time maintaining a dedicated workout regimen. Between work, travel, and social commitments, keeping a predictable schedule of gym visits may seem nearly impossible.

Walking is the most prevalent and preferred method of physical activity for both work and leisure purposes, thus making it a prime target for physical activity promotion interventions. Step-counting devices (referred to in general as pedometers/accelerometers) are known, which, being carried by a user, enable measurement of the number of steps made, and calculation of the distance traveled, as well as supplying of additional information, such as, for example, the average speed, or the consumption of calories.

Although the invention of the pedometer is commonly attributed to U.S. President Thomas Jefferson, drawings from the 15th century indicate that Leonardo da Vinci was the conceptual originator (Gibbs-Smith, 1978). His early design appeared to be a gear-driven device with a pendulum arm designed to move back and forth with the swinging of the legs during walking.

Pedometers have been used in Japan to assess physical activity and increase walking behaviors for over 30 years. It is reported that a pedometer came onto the commercial market in 1965 under the name of manpo-meter (manpo in Japanese means 10,000 steps). Both the slogan and the pedometer were widely accepted by the public and organized walking clubs seized the concept. (Hatano, Y. Use of the pedometer for promoting daily walking exercise, Int Council Health, Phys Ed, Rec. 29 (1993), pp. 4-8.). Hatano reported that surveys conducted at walking events in Japan indicate that >90% of respondents have been aware of the slogan for more than five years and each household reports ownership of almost 2 pedometers.

When carried along with a standard pedometer, such a collection of single-purpose devices often results in inconvenient bulk, particularly for exercising runners and walkers who prefer not to be encumbered in such a manner. Additionally, leg-worn pedometers are difficult to read while moving, such that the user who wishes to know his progress must interrupt his walk, run, or jog in order to check the pedometer reading. An attempted solution has been to combine single-use devices into one multi-purpose device so that a person need carry fewer accessories.

Wireless telephones, personal data assistants, and music players of various kinds, for example, have all become standard equipment for many people regardless of their activity of the moment. Combining a pedometer with a primarily hand-held device such as a mobile phone may cut down on the number of devices carried. With the small form factor, which the MEMS (Micro Electro Mechanical System) technology has made possible, accelerometers are increasingly becoming as standard hardware components in feature rich mobile phones and PDAs. Mobile phones have long been recognized as an ideal platform for pervasive applications. They are increasingly seen as a platform of choice for urban and people-centric sensing systems. They are well suited for this domain due to their ubiquity, expanding suite of sensors and ability to interact with additional external sensors via short range radiofrequency transmission. Further, given the increasing market penetration of cellular phones and the parallel trend of sole reliance on cell phones for telephonic service, they are likely to be carried at all times. Data collection and sharing via cell phones and similar mobile devices are key enablers of the instant invention. Beyond game play and screen orientation, the most popular uses for 3-axis MEMS accelerometer motion sensors in phones include power management, shake modes for control of tracks in music phones, context awareness, pedometers, so on and so forth. Therefore majority of mobile handsets introduced in the market during 2009 integrate MEMS accelerometer chips.

A cell phone may be carried in any number of locations on a person's body, such as on the belt, on an arm band, in a jacket pocket, or in the hand while talking. Such a variety of possible locations presents extreme difficulty in calibration and activity tracking, and can result in false positives or other data anomalies. Even if the device is worn in the same place through the entirety of the day, such as on the user's belt, the user will often have to move the device to check his or her progress, thus potentially providing more false positives or resulting in further lost data.

In conclusion, the value of regular physical activity and dietary regulation is now clearly established in pathogenesis of chronic diseases. Although lifestyle change has significant prophylactic/therapeutic role in controlling chronic diseases and definite advantage over the toxic prescription drugs, it is hardly exploited in everyday practice by clinicians. This is because there is no precise method to prescribe, administer, monitor and measure the quantum of dose and its effect on human health and diseases. The instant invention fills that huge void.

DESCRIPTION OF PRIOR ART

Using pedometers to measure and monitor exercise is very common. There is plenty of prior art in the use of accelerometers in designing body wearable pedometers for counting steps and converting the distance walked into energy expended. Energy consumption of a person is the sum of energy for basal metabolism just enough to maintain vital functions and energy for metabolism for living activities. "Metabolism for living activities" means the physical and chemical processes excluding basal metabolism, which are produced in the person's body when the person does daily activity, such as walking. When the amount of caloric intake of a person is greater than the person's energy consumption, the person gains weight through lack of exercise. When the person exercises excessively, the energy consumption exceeds the amount of caloric intake.

Some of the pertinent patent disclosures are as follows:

Ihashi in U.S. Pat. No. 7,526,404 and U.S. Pat. No. 7,512,517 to Tsubata teaches more accurate methods of measuring the number of steps by incorporating in pedometers separate measuring functions in walking and in running modes. U.S. Pat. No. 5,645,509, entitled "Remote Exercise Control System" discloses a remote exercise control system in which an exercise machine, such as a treadmill, remotely communicates via a communications module with an evaluation module located at a remote location. U.S. Pat. No. 6,997,852 to Watterson et al. similarly teach methods for providing a portable remote device capable of controlling the operation of the exercise mechanism while providing the exercising individual with motivational content.

U.S. Pat. No. 5,891,042 discloses a fitness monitoring device including a body motion detector (a pedometer) which measures body motion (i.e. physical activity) of the subject, and a heart rate detector which measures the heart rate, and thereby the exertion level of the subject. Itoh et al in U.S. Pat.

No. 6,506,142 describe a health maintenance system that uses a portable motion recorder and exercise machines for general health maintenance.

U.S. Pat. No. 7,062,225 to White teaches monitoring an athletic endeavor by incorporating a local area wireless transceiver to transmit performance metrics like average speed or distance traveled in either visual display or via an output mechanism such as an audio device capable of presenting the performance metric to a user in an audible message. U.S. Pat. No. 7,376,533 to Fujiwara teaches an electronic pedometer in which a step is counted only by a walk motion of a user, and not by a motion other than walk of the user.

U.S. Pat. No. 7,463,997 to Pasolini et al described a step detection method using an algorithm for self-adaptive computation of acceleration thresholds, which is based upon the comparison of the value of the acceleration signal with a reference threshold having a pre-set value for the detection of acceleration peaks. U.S. Pat. No. 7,503,476 to Bhavnani describes a compact multifunction pedometer that includes functions to determine the distance traveled, the time elapsed or remaining, and the caloric consumption during the wearer's exercise session, along with surfaces for displaying advertising.

Howell et al in U.S. Pat. Nos. 7,543,934 and 7,481,531 disclose inventions that pertain to an eyewear with activity monitoring capability, such as motion, steps or distance, measured by an activity detecting accelerometer pedometer, without the need to carry a separate electrical device.

Parks et al in U.S. Pat. No. 7,559,877 disclose an exercise measuring and monitoring device that allows the user to easily set user-specified exercise goals that are tracked by the device during exercise activity, and that allow the user to easily setup user-specified personalized notification messages that are displayed by the device upon achievement of the corresponding user-specified goals.

Mault et al, U.S. Patent App. Pub. No. 2002/0109600 discloses a wrist mounted smart activity monitor ("SAM") which is a pedometer based device that includes an electronic clock, a sensor, entry means for recording food consumption and exercise activities and a memory for storing such information. Mault also discloses a method of monitoring caloric expenditure resulting from body activity in U.S. Pat. No. 6,571,200.

Carlson in US Patent App. Pub. No. 20040176226 teaches a universal system for monitoring activities and motions during exercise and controlling the resistance provided to a user of exercise equipment during such activities, thus providing an adjustable resistance system for exercising parts of the body having complex movements over a full range of motion such as the arms, legs, neck, wrist, ankle, and torso.

LeBoeuf et al. in US App. Pub. No. 20080146892 disclose a noninvasive health and environmental monitors that include a plurality of compact physiological and environmental sensors integrated within small, low-profile devices, which wirelessly transmit physiological and environmental data to a wireless network, where the data is stored and/or processed. This information is then used to support a variety of useful methods, such as clinical trials, marketing studies, biofeedback, entertainment, and others.

Fernstrom et al. in US App. Pub. No. 20090012433 teach a method to accurately measure both food intake and physical activity by the use of a video camera and one or more physiological sensors including accelerometer. Levine et al in a recent US Pub. No. 20090048538 teach a physiological monitoring system that uses accelerometers to deploy multiple posture and activity sensing devices to detect a subject's body posture and/or activity to measure and potentially promote non-exercise activity thermogenesis.

No et al., in US Pub. No. 20080140338 disclose a mobile device-based motion detection method wherein two different sampling rates are deployed depending on the detection of motion for the purpose of conserving the limited supply of power and processing power of the device. Jorgensen in US Pub. No. 20080172203 teaches a method of enhancing the accuracy of accelerometer measurements processing of kinematic signals and removing noise from the data obtained from constantly altering orientation of the device as it is carried in user's pocket.

Nicholl in US Pub No. 20070135690 discloses a mobile communication device that provides both positive and negative health feedback to the user depending on whether the goals are achieved or not. Teller et al, in US Pub No. 20070173705 disclose a method for monitoring health, wellness and fitness by means of sensor in communication with a wearable device for monitoring and reporting the activity level and caloric expenditure of an individual.

Sysko et al. in US Pub No. 20070288266 disclose a method for managing a chronic disease in a patient. The method may comprise receiving first data and second data at a patient communication terminal, the first data being representative of the patient's physical condition and the second data being representative of the patient's readiness to modify behavior. The method may further include transmitting the first and second data over a communication channel to a disease management server, generating an output signal at the server representative of a disease treatment action based on the first and second data, transmitting the output signal over the communication channel to the patient communication terminal, and displaying the output signal at the patient communication terminal. The Sysko disclosure however neither provides means for caregiver to prescribe and monitor the exercise regimen or for payer to provide motivational reduction in patient's cost linked to compliance with the prescribed physical activity prescription.

Recently Schuler et al in Pub. No. 20090082994 disclosed a body wearable exercise monitoring system wherein the pedometer accelerometer is integrated within a headpiece, which wirelessly or non-wirelessly communicates and interfaces with a personal communications device for processing and displaying the pedometer data.

More recently Altman in Pub No. 20090176526 disclosed a method for tracking longitudinal data for the maintenance and management of health of an individual, wherein labels on numerous groceries, drugs, beverages, etc., may be read by a scanner or reader embedded in a PDA or cell phone or similar small electronic device, in addition to tracking exercise levels and energy expenditure during the day using a wireless pedometer that connects to the PDA/cell phone via Bluetooth.

Prior art pedometer accelerometer devices lack network as well as client components essential to prescribing, monitoring, measuring and motivationally enforcing compliance of a therapeutic lifestyle/physical activity regimen to enhance quality of life, and improve treatment and prognosis of morbidities in a real life healthcare delivery environment. They also lack empirical measures of the quantitative impact of lifestyle interventions on the morbidity and mortality metrics. They further lack means to engage the caregiver and the payer proactively in promoting the user's health.

SUMMARY OF THE INVENTION

The present invention addresses the foregoing need for a method of non-pharmaceutical intervention in preventing and treating chronic diseases by providing a multifunction exercise measuring and monitoring device that has a user friendly menu-driven display for monitoring performance parameters and for inputting data, that allows the caregiver/physician to easily and interactively prescribe and monitor patient-specific physical activity, lifestyle and dietary goals that are tracked by the device in real time as well as cumulatively. Accordingly, there is a need for a versatile invention as summarized herein in some detail. Consequently, it is an advantage of the invention that it comprehensively incorporates almost all the components of an ideal healthcare system ranging from prevention to education, counseling, compliance, and therapeutic, prognostic and rehabilitative interventions in most ambulatory non-terminal morbidity settings.

Such physical activity dosing device objectively measures the prescribed dose of physical activity and notifies the patient, daily, weekly and monthly compliance with personalized motivating notification messages, and also informs the physician. The device also displays a graphic representation of the reduction of patient's all-cause morbidity and mortality risks based on the physical activity and dietary targets achieved. The method provides means to proactively engage the caregiver and the payer in promoting the user's health by prescribing, implementing, dosing, monitoring and rewarding the user with incentives to alter and maintain healthy lifestyle.

It is therefore an object of the present invention to provide an entirely new method of prescribing a non-pharmaceutical therapeutic lifestyle regimen for preventing and treating chronic diseases by means of a multifunctional handheld body wearable communication device that administers, monitors, measures and ensures compliance of healthy lifestyle practices with the eventual goal of achieving minimal or zero intervention with pharmaceutical agents.

It is also an object of the present invention to prevent chronic morbidities without any pharmacological intervention (hereinafter Prescription Zero or Rx Zero). It is yet another object of the present invention to treat patients suffering from chronic diseases with an ultimate object of achieving zero pharmaceutical intervention (Rx Zero), or weaning such patients from heavy pharmaceutical intervention to minimal intervention, or improving prognosis in chronic morbidities in combination with pharmacological treatment.

It is also an object to provide a first and primary prescription device that limits the use of prescription drugs only to supplement the Rx Zero treatment until the time such medications are absolutely necessary in treatment of lifestyle related chronic diseases such as hypertension, hyperlipidemia, endothelial dysfunction, metabolic syndrome, obesity, coronary artery disease, stroke, diabetes, or certain cancers such as breast cancer, prostate cancer, colorectal cancer and pancreatic cancer.

It is also an object of the invention to provide an always-on user friendly tool to the users for adapting and maintaining healthy behaviors. It is also an object of the invention to reduce the all cause morbidity and mortality risks amongst the users of the method. It is still another object of the present invention to provide the caregiver a convenient method of prescribing and monitoring a highly regulated physical activity regimen to the patients of chronic diseases and lifestyle related morbidities. It is yet another object of the present invention to provide the patients a user friendly means of undertaking physical activity and other behavioral lifestyle changes.

It is also an object of the invention to ensure high compliance by the users to the prescribed Rx Zero lifestyle regimen by delivering motivational content and incentives to the user. It is a further object of the invention to reward successful implementation of such Rx Zero therapeutic regimen with monetary and non-monetary incentives. It is also another object of the invention to minimize the health insurance premium of the user by means of discounts for user's compliance with the Rx Zero regimen. It is further object of the invention to improve quality and lower the cost of healthcare.

It is still further object of the instant invention to transform the global sickcare system that lets people get sick first and then treat and maintain the disease with expensive pharmaceuticals, to a real healthcare that works to improve the health of the people. It is also an the object of the instant invention to provide a tool that engages all levels of caregiver including tertiary care specialists and not just primary healthcare practitioners in the delivery of Primary Health Care (PHC). It is further object of the invention to implement "Prevention" not just to prevent diseases, but to prevent lifelong dependence on prescription drugs amongst patients with chronic diseases.

It is the eventual object of the invention to remedy the failures of PHC by presenting Rx Zero as the ultimate approach that redefines the concepts of PHC and Prevention, and disseminates the obligations of PHC beyond the PHC practitioners to tertiary caregivers. Finally, it is the ultimate object of the present invention to provide a tool for achieving the WHO goal of "Health for All."

The present invention is directed to devices, systems, methods, programs, computer products, computer readable media, and modules for controlling one or more operating parameters of one or more devices by a wearable personal communication device that receives programming from a remote server or system, such as the RxZero website. The invention is particularly well suited to personal communication devices that integrate accelerometers.

These advantages in addition to other objects and advantages of the invention will be set forth in the description which follows, and in part will be obvious from the description, or may be learned by the practice of the invention. The objects and advantages of the invention may be realized and obtained by means of the software, algorithms, devices, remote servers and combinations thereof particularly pointed out in the appended claims.

BRIEF DESCRIPTION OF THE DRAWINGS

FIG. 1. Orientations Showing Directions for Each Accelerometer Axis in a Composite Rx Zero Device.

FIG. 2. External Accelerometer Transmitting XYZ Axes Data to the Rx Zero Device in a Segregated Rx Zero Embodiment.

FIG. 3. Network Architecture of Composite Rx Zero Device: Integrated MEMS Sensor.

FIG. 4. Network Architecture of Segregated Rx Zero Embodiment: External Accelerometer.

FIG. 5. Exemplary Block Diagram Illustrating Flow of Distributed Data Processing.

FIG. 6. First Embodiment: Rx Zero Composite Device Networking.

FIG. 7. Second Embodiment: Rx Zero With Spatial Displacement Filtering When Used With Conventional Treadmill.

FIG. 8. Third Embodiment: Rx Zero Device Networking With Treadmill's Wireless Pedometer.

FIG. 9. Fourth Embodiment: Segregated Rx Zero with External Accelerometer.

DETAILED DESCRIPTION OF THE INVENTION

It is advantageous to define several terms before describing the invention. It should be appreciated that the following terms are used throughout this application. Where the definition of terms departs from the commonly used meaning of the term, applicant intends to utilize the definitions provided below, unless specifically indicated. For the purpose of describing the instant invention following definitions of the technical terms are stipulated:

1. Accelerometer: An accelerometer is an electromechanical device that measures acceleration forces. These forces may be static, like the constant force of gravity, or they could be dynamic—caused by moving or vibrating the accelerometer. As used in this invention the term implies a small form factor physical activity sensing MEMS (Micro Electro Mechanical System) chip. MEMS is the integration of mechanical elements, sensors, actuators, and electronics on a common silicon substrate through microfabrication technology. An accelerometer may be single axis, dual axis or triple axis accelerometer identified as X, Y, and Z axes.

2. Pedometer: A pedometer is an accelerometer based device, which measures the distance by recording the number of steps when carried by a user. The pedometer may also include an algorithm to estimate calories burnt based on the distance traversed by the user.

3. RF Module: An RF Module within the meaning of the description of the instant invention is a hardware which is capable of either generating and transmitting high frequency radio waves or receiving and reading high frequency radio waves for the purpose of wireless communication or wireless data transfer between two or more devices. The RF (radiofrequency) transmitter is also called as RF transponder and the RF receiver is also called as RF transceiver/reader. Such RF Modules are integrated within the devices to establish wireless communicability between them. The high frequency radio waves deployed by such RF Modules for communicating with each other are usually within the 3 MHz to 30 MHz range. When RF Transceiver Module detects an RF Transponder Module in its vicinity, which usually ranges between 1 cm and 10 ft, it automatically initiates a communication link. Bluetooth is a common example of an RF module.

4. Health: "Health is a tangible and dynamic state of human wellbeing in ever changing physical and metaphysical realm of four dimensional space-time continuum in which the human host and the disease causing agent continuously interact in an environment of physical, social, cultural, educational, spiritual, economic and political ecosystem, wherein the probable occurrence of any and all types of direct or indirect causal indicators of morbidities, mortalities and infirmities are proactively, preemptively and sustainably restrained at least two sigma (standard deviation) limits outside of the reference normality."

5. Health Insurance & Premium & Policy: Insurance is a form of risk management primarily used to hedge against the risk of a contingent loss. Insurance that pays for medical expenses is termed as health insurance. It may also include insurance covering disability or dismemberment. In the developed nations, Health Insurance is the norm rather than an exception for average citizens. It may be purchased on a group basis (e.g., by a firm to cover its employees) or purchased by individual consumers or an employer may self-fund the health insurance coverage to his employees. In each case, the covered groups or individuals pay premiums or taxes to help protect themselves from high or unexpected healthcare expenses. By estimating the overall risk of healthcare expenses, a routine finance structure (such as a monthly premium or annual tax) is developed, ensuring that money is available to pay for the healthcare benefits specified in the insurance agreement. The benefit is administered by a central organization, most often either a government agency or a private or not-for-profit entity operating a health plan. An insurance policy is an insurance contract issued by the insurance company in consideration of the premium paid by the insured/beneficiary that determines the legal framework under which the features of the insurance contract are enforced.

6. Prescription: Prescription conventionally implies a written instruction by a qualified medical practitioner to pharmacist to dispense specific medication, and to a patient to intake that specific drug or drugs, in specified doses, for a specified length of time. A prescription largely implies a pharmaceutical intervention. However within the meaning of the instant invention, prescription refers to prescribing non-pharmaceutical intervention that deploys regimented and device-measurable lifestyle alterations that include physical activity and behavioral changes involving habits and diets. It not only includes the prescription for treatment but also a prescription for prevention and rehabilitation. Rx is an abbreviation for prescription and usually precedes the description of the treatment advised by the clinician.

7. Rx Zero/Prescription Zero: Rx Zero is a new terminology used in the specification to illustrate the ultimate objective of the method of the instant invention, which is to eventually achieve zero pharmacological intervention in preventing or treating chronic morbidities by means of a regimented and measurable lifestyle alteration that includes dietary control, behavioral changes such as cessation of smoking and substance abuse, and device measured and monitored physical activity goals. Rx Zero can therefore be defined as a completely non-pharmaceutical user-friendly, device-aided, regimented and measurable lifestyle behavior modifying intervention, which avoids, minimizes or eliminates the prescription of pharmaceutical agents in management of chronic morbidities, and which is prescribed as the first and primary prescription, limiting the use of prescription drugs only to supplement the Rx Zero treatment until the time such medications are absolutely necessary in treatment of lifestyle related chronic diseases such as hypertension, hyperlipidemia, endothelial dysfunction, metabolic syndrome, obesity, coronary artery disease, stroke, diabetes, or certain cancers such as breast cancer, prostate cancer, colorectal cancer, pancreatic cancer so on and so forth.

For the purpose of describing the merits of this invention and its role in transforming the sick care system to real healthcare system the term Rx Zero is appropriate, convenient and frequently used in describing the invention. It encompasses not only the prevention component by eliminating the future need for pharmacological interventions, but also includes the therapy component after the chronic disease has actually been diagnosed. In the former the disease onset is prevented before it sets in, while in the later situation it targets the lifelong drug usage to minimal or zero by deploying the lifestyle changes as the first line of treatment and prescription drugs only to supplement and support the first line of treatment. Therefore, Rx Zero clearly expands the conceptual meaning of "PHC" or "Prevention Programs" from currently understood meaning of merely prevention of morbidities, to include prevention of long term adverse effects of chronic pharmacological interventions amongst ambulatory patients without terminal diseases.
8. Rx Zero Composite Device: A handheld interactive communication device (also consumer device or PDA or mobile phone or wearable computer) with integrated MEMS accelerometer chip for receiving Rx Zero prescription from a medical practitioner in real time, and administering, measuring, quantifying, monitoring, motivating and implementing 24/7, a comprehensive lifestyle behavioral modification approach involving therapeutic physical activity and related dietary lifestyle changes. Rx Zero device also communicates to the user, health benefits of the Rx Zero regimen in terms of risk reduction for future morbidities/mortalities, prognosis for current morbidities, and progression towards the Rx Zero objective of weaning out or complete elimination of the long term pharmaceutical drugs, and rewards therein for achieving the prescribed lifestyle targets.
9. Rx Zero Segregated: A handheld communication device (consumer device or PDA or mobile phone) with external MEMS accelerometer, both equipped with RF Modules capable of connecting with each other wirelessly. The user can wear or carry both the devices on his person for receiving Rx Zero prescription from a medical practitioner in real time, and for administering, measuring, quantifying, monitoring, motivating and implementing 24/7, the Rx Zero method as illustrated in the preceding paragraph.
10. Ambulatory patient: The term "ambulatory patient" refers to all users of the method and device of the instant invention, who are not bedridden or with incapacitated mobility whether suffering from a chronic disease or otherwise healthy at risk of one or more morbidities.
11. Free living: The term is used as an adjective in describing either a user of the Rx Zero method of the instant invention who is ambulatory and who uses the device continuously 24/7 in natural uncontrolled environment without having to switch it on or off, or it also refers to the physical activity/lifestyle parameter measurements that are recorded by the Rx Zero device in natural uncontrolled environment during the normal course of the user's daily routine.
12. Morbidity, Mortality & All-Cause Morbidity/Mortality Rates: Morbidity refers to a diseased state, disability, or poor health due to any cause. The term may be used to refer to the existence of any form of disease, or to the degree that the health condition affects the patient, including physiological risk factors such as hypertension, hypercholesterolemia, obesity, so and so forth. Morbidity rate is the incidence of a particular disease or disorder in a population usually expressed as cases per thousand. Mortality refers to deceased state resulting from death. Mortality rate is a measure of deaths in a given population. All-cause morbidity/mortality rates refer to total morbidity/mortality per annum per thousand individuals in a given population resulting from any and all causes.
13. Rx Zero Diet: There are many different diet protocols available in the prior art for maintaining good health. A typical Rx Zero diet can be based on any of the prior art diet protocols that includes a high fiber low calorie diet that is not less than 10 calories per pound of body weight and not more than 15 calories per pound of body weight, and includes diet with high intake of fruits, vegetables, nuts and legumes, whole grains and low-fat dairy products, and low or no intake of sweetened beverages, processed foods and red meat. Additional Rx Zero diet may include no or moderate alcohol intake, no cigarette smoking, no tobacco chewing, no substance abuse, use of non-narcotic analgesics less than once per week, and intake of 400 µg/day or more of supplemental folic acid.
14. M.E.T.: MET (metabolic equivalent of task) is a physiological concept expressing the energy cost of physical activities as multiplies of Resting Metabolic Rate (RMR) and is defined as the ratio of metabolic rate (and therefore the rate of energy consumption) during a specific physical activity to a reference metabolic rate at rest obtained during quiet sitting. One MET is equal to the amount of energy expended at rest. Two definitions of the MET are essentially equivalent:
   1 MET is equivalent to a metabolic rate consuming 3.5 milliliters of oxygen per kilogram of body weight per minute.
   1 MET is equivalent to a metabolic rate consuming 1 kilocalorie per kilogram of body weight per hour.
   MET values of physical activities range from 0.9 (sleeping) to 18 (running at 17.5 km/h). For example, the intensity of walking 3 miles per hour ("mph") is about 3.3 METs. At this speed, a person who weighs 132 pounds (60 kilograms) will burn about 200 calories per hour (60.times.3.3=198).

THE EMBODIMENTS

The novel features of the Rx Zero non-pharmaceutical lifestyle intervention for preventing and treating chronic diseases of the instant invention can be deployed in any lifestyle prescription scenario whether for preventing and minimizing the risk for chronic diseases, or for maintaining a disease-free healthy lifestyle, thereby eliminating or minimizing the need for future pharmaceutical intervention, or for treatment of a chronic disease with an intent to wean the patient to minimal prescription drug use or completely eliminate the drug use; or in combination with pharmaceutical agents, improve the prognosis of the disease under treatment. The only caveat is that the user is ambulatory and capable of standing on his/her feet and walk without pain or incapacity. Accordingly several embodiments of the instant invention can be implemented, four of which are illustrated in the block diagrams of a network architecture presented in self explanatory drawings in FIGS. 6 through 9. See FIG. 6-FIG. 9.

In the embodiments described herein, all client-server data transfer between the wired or wireless nodes is implemented either through the telecommunication network or the Internet, using protocols such as but not limited to SMPP (short message peer-to-peer protocol) or WAP (Wireless Application Protocol) or HTTP or TCP/IP. Communication to and from the user's Rx Zero wireless communication device preferentially takes place according to the availability of the 802.11 and cellular data channels. For devices that support multiple communication modes, communication is attempted first using a TCP/IP connection over open 802.11 channels, second using GPRS-enabled bulk or stream transfer, and finally SMS/MMS is used as a fallback.

All peer to peer communication between the wireless nodes, when the accelerometer hardware is not incorporated within the user's handheld device, takes place via radiofrequency transmission (RF) between the RF Modules embedded within the user's handheld communication device and the external accelerometer device placed within the radiofrequency range of each of the devices.

As represented in FIG. 1 and FIG. 2 the accelerometer module can be either integrated within the user's handheld communication device 10, or it can be external 26 to the communication device 24. When the accelerometer module is external, it communicates with the handheld communication device using RF (radiofrequency e.g. Bluetooth) 28.

FIG. 1 is a graphic representation of a Composite Rx Zero Device in which a triple axis MEMS accelerometer chip is integrated within a personal communication device, and which detects and measures motion in six directions viz. X+ (forward) 12, Y+ (right) 14 and Z+ (up) 16 representing forward/positive acceleration; and X−(backward) 18, Y− (left) 20 and Z− (down) 22 representing reverse/negative acceleration.

FIG. 2 is a block diagram of Segregated Rx Zero paraphernalia, which comprise of a personal communication device 24 with RF Module but without MEMS accelerometer chip, and an external wireless MEMS accelerometer device 26. The RF Modules within the two devices establish wireless link between the devices to transmit the data generated by the X, Y and Z axes of the external accelerometer device using RF transmission 28 to the personal communication device for further processing.

The Sensor Module 30 of the instant invention comprises of a MEMS chip, whether external or internal, or whether single, double or triple axis accelerometer Hardware Sensor Sub-Module 32. The external accelerometer or Hardware Sensor Sub-Module may be resident in a disparate wireless device attached to user's body, or to user's apparel, or to a personal communication device carrying case, or to the exercise apparatus such as a bicycle or a treadmill, in each of which case it communicates wirelessly with the handheld communication device using close range radiofrequency transmission.

The Sensor Module also includes a Software Sensor Sub-Module 34. Software sensors usually measure artifacts of other software that runs on the computing platform in an effort to understand the context of the user's behavior, mood, etc. They do not sense physical phenomena but rather sense electronic footprints left as the user goes about his daily routine. Examples of virtual software sensors include, a trace of recent/current URLs loaded by the web browser, a trace of recent songs played on the music player to infer mood or activity. In the present context it is a device activity sensing software application that monitors user's usage of the different functions of the handheld communication device. Such functions are analyzed to provide the user's free living lifestyle that includes sleep patterns, physical activity patterns, socializing patterns, and also to provide greater accuracy of the accelerometer measurements by switching the accelerometer to sleep mode when the device is connected to the external power source for charging or when the user goes to sleep.

The processing and analysis of the raw data generated by the Sensor Module is distributed over more than one location to optimize the limited processing power of the Rx Zero devices. FIG. 3 and FIG. 4 illustrate an overview of the different local and remote modules involved in the distributed processing and analysis of the accelerometer data in Composite Rx Zero and in Segregated Rx Zero devices respectively. Such distributed processing not only helps best utilization of the limited processing power of the Rx Zero devices, but makes the cumulative data available for any Web based handling of the data. This is accomplished by the Sensor Data Analysis Module (or just Analysis Module), which is a client-server application that has a client-resident Local Analysis Sub-Module 36 and a (Back End Server) 38 remote server-resident Global Analysis Sub-Module 40 operating in tandem to analyze the free-living data, former at the location where the accelerometer data is generated, and later at one or more remote locations where servers with large processing power are located respectively. The output of such distributed analysis is made available in real time as user readable outcome that includes steps walked, calories consumed, morbidity risk reduced, treatment prognosis improved, prescription compliance achieved, health insurance premium reduced so on and so forth 42.

In addition to hosting the Global Data Analysis Sub-Module, the Back End Server also hosts a Sensor Data Repository 44, which is a database of users' current and cumulative activity data generated by the hardware 32 & 26 and software 34 sensors of the Sensory Module 30, and also hosts user profiles that include user's personal health-related information such as age, sex, smoking, substance abuse, dietary habits, body mass index, morbidities, etc. Such Sensor Data Repository interfaces with the other modules in the Rx Zero network to provide the data anytime for reference, inference, analysis, action and for displaying the output. The remote server also hosts the Caregiver Services Module 46, which is a World Wide Web enabled server application that allows the authorized doctor, nurse or related paramedic from the caregiver healthcare infrastructure, to prescribe, monitor, alter, counsel or remind prescription compliance of the patient's lifestyle activities through a Web browser interface from any client computer 50 or communication device connected to the Internet by means of either direct audio or instant text messages or by means of changes in the data repository module (database) via active server pages (ASP).

The Payer Services Module 48, which is also a World Wide Web enabled server application deploying actuarial algorithm that allows the third party payer/insurer of the healthcare services to automatically estimate changes in patient's health insurance premium based on the changed health parameters analyzed by the data analysis module and authorize corresponding alteration in the health insurance premium automatically or manually through a browser interface from any client computer 50 or communication device connected to Internet via TCP/IP 52.

FIG. 5 illustrates further details of the distributed data processing feature of the instant invention. The transducers X, Y & Z 52 sense motions in all directions and sends the motion data to signal processing application 54 within the Local Analysis Module of the Rx Zero device. As the Rx Zero device is always carried with the user, it is constantly exposed to variety of motions, many of them do not attribute to actual walking or running and therefore does not count in measuring actual physical activity for the purpose of estimating distance walked or calories burnt. For example a user may often remove the device from his pocket or belt mounted carrying case when there is an incoming call or when he wants to make a voice call. Similarly the transducers may record motion when the user is driving or riding a bike or traveling in a train or aircraft. Such motion data is unwanted noise that confounds the measurement of actual steps taken by the user. Another source of noise that may confound and distort the actual physical activity measurement is walking on a treadmill. For every step recorded by the positive axes of the transducers there is an equal reverse acceleration recorded by the negative axes. Such confounding data not only creates noise that destroys the accuracy of measuring the longitudinal acceleration on account of human stride, but it generates a huge amount of unwanted garbage information that may choke up the processing power of the device processors. Therefore it is imperative to use filters to sieve out the garbage. This is done, firstly, by maintaining a library of generic human stride patterns and the user's specific stride pattern 56; and secondly, by deploying a series of vector filters 58. In general human stride has cyclic vector parameters of longitudinal acceleration in two axes that are distinctly distinguishable from other acceleration patterns. Such pattern of acceleration in X, Y and Z axes for the two dimensional human stride pattern is stored in the memory and retrieved by the vector filters. If the velocity, direction and rhythmicity of the motion sensed by the accelerometer transducers fall outside the accepted range of the reference parameters the data is ignored and not accounted as a physical activity of the user.

The signal processing application processes longitudinal acceleration data in at least two axes to characterize a human stride and validates by the reference pattern stored in the reference library. The data generated by other axes are filtered out by the various filtering elements in course of such human stride validation process. Uniform single axis non-stride patterns of linear accelerations exceeding 4 miles/hour in a short time indicate vehicular motions, which confound the human walk measurements. The velocity filter 60 ignores such uniformly linear high speed vehicular accelerations. Similarly perpendicular 62, backward (reverse) 64 and gravity 66 accelerations also are caused by motions other than a human walk or run, which are filtered by corresponding filters. Most importantly, an Rx Zero device is a free living wearable personal communication device that cannot be always positioned in a particular orientation to record human stride motion in a specific accelerometer axis. Any of the X, Y, Z axis can function as the longitudinal axis in which the user walks. Re-orienting the recording axes is very important to filter out the rest of the confounding data. This is done by the human stride orientation filter 68. Finally the anti-aliazing provided by the filtering element 70 generally reduces or prevents aliasing caused by sampling of the signals provided by, or derived from, one or more accelerometer axes. Such anti-aliazing also updates the output of all these filters at their respective sample rates to optimize the application processor time, since only the relevant recording axes needs to be run at the highest sample rates.

Thus the pattern and magnitude of strides is further processed to estimate the cumulative distance traversed in number of steps or kilometers or miles, which data is transmitted to the Central Server 38 and stored in the Sensor Data Repository 44 for further global analysis. As discussed in some detail subsequently, using the biometric data relevant to the user, such as height, weight, age and other morbidity, compliance and actuarial metrics profiled from the Data Repository 44, the Caregiver 46 and the Payer Services Modules 48, provided by the remote central server, the Local Analysis Sub-Module estimates energy consumption 72 associated with the given physical activity 74, and chronic disease risk reduction ratio 76, and reduction in premium of the user's health insurance plan as one of the rewards 78. All the user metrics are combined with the device-measured free living lifestyle routines that include sleeping, resting and activity patterns, and user-profiled lifestyle traits that include smoking, drug use, dietary habits, body mass index and morbidities, to estimate various health indices that define the therapeutic lifestyle targets achieved, morbidities reduced and prognosis improved in a user readable health status dashboard formatted in a GUI, on the output inlay of the user's handheld communication device 10 and 24, and also via an active server webpage accessed through any computer connected to the Internet 80.

The core of the Rx Zero network architecture resides on a single or a set of remote servers that hold a database of users 44, caregiver module 46 and payer module 48 and of course the global analysis sub-module 40 collectively termed as Back End Server/s 38. The access to the Rx Zero network is implemented as a Web portal that provides access and data input rights via GUI to user specific computer terminals depending upon whether the access is provided to the patient user 10 and 80, to a caregiver clinician/nurse/paramedic 82, to a payer representative 84, or to the system administrator 86. Such network access deploys security protocols to securely login 88 to the Back End Server. Each of these user accounts contain algorithms to draw inferences about many objective and subjective aspects of the Rx Zero user/patient/subscriber/beneficiary, some of which were described earlier and others are discussed herein.

The Data Repository 44, which serves as the database of not only the hardware and software sensor records, but complete biometric, diet and behavioral profiles of all the users 90, which provides a feed to all the other modules in the Rx Zero network for further use and analysis. Such database deploys fusion 92 and clustering 94 techniques for global analysis of the data. The database also feeds the Caregiver Module 46 and Payer Module 48. The caregiver uses the caregiver 10 terminal 82 to access the Web interface for prescribing, reviewing or revising the Rx Zero therapeutic dose 96. Such review or revision of the therapeutic dose prescribed by the caregiver takes into account the level of compliance 98 and its impact on all cause morbidity/mortality risk 100 and on prognosis of the treatment 102 based on the real time status of user's profile and sensing data. The payer can also use an Insurer Administration Web interface 104 for underwriting policy and reviewing or revising the policy premium 106 by deploying actuarial algorithm 108 to real time data pertaining to the status of user's profile, compliance to Rx Zero therapy, morbidity/mortality risk and prognosis of the ongoing treatment.

Based on the physical activity recorded by Rx Zero device of the present invention, there are several ways known to the prior art to measure the expenditure of energy. The number of steps may be used to calculate the miles/hour. Approximately 2000 steps constitute a mile, and using the user's body weight as the multiplier, calories burnt can be estimated using prior art methods. The total daily calories intake and expenditure is estimated based on the therapeutic need and profile of the user. For example an average non-obese user may not need to burn more calories than calories consumed, whereas an obese user vice versa. Accordingly the calorie consumption and the physical activity prescribed can be adjusted for the desired optimal effect. In most cases however, the dietary goal of the Rx Zero includes a high fiber low calorie diet that may usually range between 10 and 15 calories per pound of body weight, and includes diet with high intake of fruits, vegetables, nuts and legumes, whole grains and low-fat dairy products. Sweetened beverages, processed foods and red meat are either eliminated or consumed minimally.

The Rx Zero therapeutic dose of physical activity is prescribed based on general condition of the user, current level of physical activity and activity limiting co-morbidities present. A typical Rx Zero prescription regimen in most cases of a completely sedentary but ambulatory user on low calorie diet may begin with 20,000 steps per week for the first four weeks, then increased to about 40,000 steps per week for the next four weeks and finally maintained at a level between 50,000 and 70,000 steps per week permanently thereafter.

Furthermore, the physical activity and energy consumption may also be measured in terms of a physical activity metric, which is very well known to the prior art—METs (Metabolic Equivalents of Task). A typical Rx Zero prescription may set goals of 500 MET-minutes per week for the first four weeks, about 1,000 MET-minutes for the next four weeks and finally achieving maintenance of 1,200 to 1,800 MET-minutes permanently thereafter.

The benefits of achieving the Rx Zero goals include:
a) to the individual user/patient, monitory benefits such as reduction in the health insurance premium corresponding to the levels lifestyle change reached, and non-monetary rewards such as improved health, reduce morbidity/mortality risk, reduced or eliminated prescription drugs, improved treatment prognosis, better patient-caregiver interaction, motivational messages and promotional offers;
b) to the community, improved health status with good quality healthcare at lower cost to the economy;
c) to the caregiver and policy makers, an effective tool that disseminates and implements "Primary Health Care" and "Prevention" at all levels of healthcare and beyond the currently understood scope of these terms that limits responsibilities to the primary care practitioners; and;
d) to the payer, decline in loss ratio on account of reduced claims.

The First Preferred Embodiment

The first preferred embodiment of the invention is illustrated in FIG. 6 as it would be implemented in a normal walking or jogging scenario using the composite Rx Zero device 10. The method typically may begin with a caregiver physician or authorized nurse/paramedic using his/her office computer 82 to prescribe an Rx Zero therapy regimen to the user, which he receives on his mobile phone 10. The user accepts the Rx Zero regimen, which is downloaded to his mobile phone as a thin client. The user signs up for an account either from the mobile phone itself or from his home computer 80. Prior to initializing the Rx Zero regimen the user may be requested to calibrate the device by walking a short distance to obtain a predictive algorithm tailored to his walking style. Such reference algorithm is stored in the device library of reference patterns 56 for accurate signal processing and noise filtering. Once the user is ready to start complying with the prescribed regimen, he walks or jogs 110 with his Rx Zero device 10 either in his pocket or mounted on his waist belt. Communication to and from the user's Rx Zero wireless communication device preferentially takes place according to the availability of the 802.11 and cellular data channels. For devices that support multiple communication modes, communication is attempted first using a TCP/IP connection over open 802.11 channels, second using GPRS-enabled bulk or stream transfer, and finally SMS/MMS is used as a fallback. Using one of these modes of communications, the Rx Zero device intermittently sends data which is locally analyzed 36, to the Bank End Server 38 for further global analysis 40 in tandem, and for storing it in the Data Repository 44 database for subsequent reference, retrieval and analyses.

While the user continues to comply daily with his prescribed Rx Zero regimen, his progress is monitored 24/7, and he regularly receives progress reports and motivational input from the caregiver 82, payer 84 and system administrator 86 on a regular basis as necessary for ensuring compliance. Additionally the assessment of various health indices that define the therapeutic lifestyle targets achieved, morbidities reduced, and prognosis improved are presented in GUI to him in real time in a user friendly health status dashboard on the output inlay of the user's handheld communication device 10, and also via an active server webpage accessed through a user computer 80 connected to the Internet. Additionally, as a consequence of continued compliance with the regimen the user's health status improves resulting in lowering of his health insurance premium.

The Second Preferred Embodiment

The second preferred embodiment of the invention is illustrated in FIG. 7 as it would be implemented using a conventional treadmill. The method begins and proceeds in the same way as the first preferred embodiment except that user uses a conventional treadmill for walking/jogging 112. The composite Rx Zero device 10 can be mounted on the waist, in the pocket or on one of the legs or just stuck into the socks. If the device is mounted on the leg, the measurement confounding on account of alternate negative acceleration with every step is huge. In treadmill the user walks on a belt that moves backward as the user walks forward but never changes his position relative to the treadmill, therefore actual net spatial displacement is absent in treadmill walk. For a step taken by the first leg there is a forward acceleration, but as the user moves the second leg forward the first leg is brought to its original location by the backward velocity of the treadmill belt 114. Therefore in every pair of steps the accelerometer senses a forward velocity and a corresponding paired backward velocity, which result in unchanged position of the user. The backward vector filter algorithm 64 annuls the backward acceleration and lets the signal processing application record only the forward acceleration. Thus the Rx Zero device automatically adjusts for the noise on account of the treadmill artifacts. Rest of the analysis is the same as in the first preferred embodiment.

The Third Preferred Embodiment

The third preferred embodiment of the invention is illustrated in FIG. 8 as it would be implemented using a treadmill 116 equipped with a matching radiofrequency (RF) wireless pedometer 118 such as Bluetooth. The method begins and proceeds in the same way as the first and second preferred embodiments except that the wireless pedometer of the treadmill is capable of communicating with the user's composite Rx Zero device's wireless module. On detecting the RF signals from the treadmill mounted wireless pedometer and the alternate negative/positive acceleration pattern of the treadmill, the Local Analysis Sub-Module of the user's Rx Zero device triggers an automatic override to ignore the local accelerometer data, and instead accept the acceleration data from the wireless treadmill pedometer. Thus Rx Zero readings are reconciled with the treadmill readings. Rest of the analysis is the same as the first and second embodiment.

The Fourth Preferred Embodiment

The fourth preferred embodiment of the invention is illustrated in FIG. 9 as it would be implemented in a normal walking or jogging scenario using the Segregated Rx Zero device 24, wherein the MEMS accelerometer device is external 26 and connects wirelessly to the Rx Zero device using RF (radiofrequency e.g. Bluetooth) 28. When the two devices are mounted on the same person in proximity as shown in FIG. 9, the RF Modules within the two devices establish wireless link between the devices to transmit the data generated by the X, Y and Z axes of the external accelerometer device using RF transmission 28 to the Rx Zero device for further processing. Rest of the method proceeds in the same way as the first preferred embodiment, and features and benefits are the same as already described with the first embodiment.

Other Embodiments

The present invention can also be adapted to situations such as riding a bicycle, or using an exercise-equipment equipped with wireless pedometer or calorimeter device. Such embodiments are similar to the features of the Third Embodiment described in preceding paragraphs. As long as the wireless device is set up to output the result of physical activity in terms of calories burnt, the Rx Zero device of instant invention will receive that information overriding its own vector measurement for that duration, and accordingly convert the data and add it to the prescribed dose so as to readjust the balance of the remaining amount of physical activity due for that day.

Furthermore, the invention can also be adapted to be deployed in non-disease circumstances, wherein the demands of physical activity and diet may be different than in normal situations. For example in obstetrics and gynecology practice, growing evidence suggests that complete immobility or bed rest is more physically devastating to an expectant mother than one would expect. Sedentary mothers may suffer loss of muscular and cardiovascular fitness, excessive weight gain, higher risk of gestational diabetes, pregnancy-induced hypertension, varicose veins, dyspnea, low back pain, poor psychological adjustment to the physical adjustment of pregnancy, worsening obesity and consequently increased risk of complications and the risk of cesarean. A regular exercise regime during pregnancy can not only help expecting mothers with their body image, but also protect them from depression. Studies have also shown that women who exercise regularly delivered healthier babies with a strong fetal heart rate. Research also suggests that women, who exercised, had easier pregnancy and delivery, and spent a third less time in labor. The method of the instant invention can be easily adapted for administering and monitoring measured optimal amounts of physical activity to mothers, pre, post, and during pregnancy.

The description of the present invention has been presented for purposes of illustration and description, and is not intended to be exhaustive or limited to the invention in the form disclosed. Many modifications and variations will be apparent to those of ordinary skill in the art. The embodiments were chosen and described in order to best explain the principles of the invention, practical applications, and to enable others of ordinary skill in the art to understand the invention and its various modifications as are suited to any specific use contemplated.

The invention claimed is:

1. A non-pharmaceutical method and prescription device for achieving a goal of zero drug intervention (Rx Zero) in treatment and prevention of chronic diseases by means of prescribing, administering, measuring, quantifying, monitoring, motivating and implementing a lifestyle behavior modification approach involving therapeutic physical activity and related dietary and behavioral lifestyle changes resulting in consequent health benefits in terms of risk reduction for future morbidities and mortalities, prognosis for current morbidities, reduction, weaning out, or elimination of chronic pharmaceutical intervention, and rewards accruing for achieving a prescribed lifestyle goal, comprising of:
   a) either a wearable or a handheld communication device or a personal user device, which may be a mobile wearable computer, a PDA or a mobile phone that is capable of performing, recording and displaying data regarding user's free-living lifestyle usage of functions pertaining to telecommunication, surfing Internet, playing music, power management, recording physical movements, and recording periods of inactivity that occurs during user's sleep or during a period the device is connected to external power source for charging;
   b) a sensor module comprising of the following two sensor sub-modules:
      i. a first sensor sub-module wherein the said sensor is a physical activity sensing MEMS (Micro Electro Mechanical System) single, double or triple axis accelerometer hardware sensor and a device activity sensing software sensor application either integrated within a hand held communication device or a mobile wearable computer or a PDA or a mobile phone, or resident in a disparate wireless device attached to user's body, or to user's apparel, or to a personal communication device carrying case, or to an exercise apparatus such as a bicycle or a treadmill, in each of which case the first sensor sub-module communicates wirelessly with a mobile wearable computer, or a handheld communication device, or a PDA or a mobile phone using close range radiofrequency transmission, and,
      ii. a second sensor sub-module wherein the said sensor is a software client server application that monitors user's usage data regarding different functions of a mobile wearable computer, or a handheld communication device, or a PDA or a mobile phone, that is analyzed to provide the user's free-living lifestyle that includes sleep patterns, physical activity or inactivity patterns, socializing patterns, mood patterns, and also to provide greater accuracy of accelerometer recordings by switching the accelerometer to sleep mode when the device is connected to the external power source for charging or when the user goes to sleep.
   c) a distributed sensor data analysis module, which is a client-server application that has a client-resident local analysis sub-module and a server resident global analysis sub-module operating in tandem to analyze free-living sensing data generated by the sensor module, and output as user readable outcome that includes steps walked, calories consumed, morbidity risk reduced, treatment prognosis improved, prescription compliance achieved;
   d) a central server or data repository module, which is a database of user profiles that include user's personal health-related information such as age, sex, smoking, substance abuse, dietary habits, body mass index, morbidities, and corresponding sensor module-sensed user activities that the user of one or more of the said sensor modules can securely access and utilize for reference, inference, analysis, action and display;
   e) a caregiver services module, which is a World Wide Web enabled server application that allows an authorized doctor, nurse or related paramedic from a caregiver healthcare infrastructure, to prescribe, monitor, alter, counsel or remind prescription compliance of user's lifestyle activities through a Web browser interface from a client computer or communication device connected to Internet by means of either direct audio or instant text messages or by means of changes in data repository module;
   f) a payer services module, which is a World Wide Web enabled server application deploying actuarial algorithm that allows a third party payer of healthcare services or an health insurer to automatically estimate changes in patient's health insurance premium based on a changed health parameters analyzed by the data analysis module and authorize corresponding alteration in health insurance premium automatically or manually through a browser interface from a client computer or communication device connected to the Internet;

g) a user health status dashboard GUI module, which displays user's health indices in a form of distance traversed and calories burnt, and combines the said health indices with sensory module-measured lifestyle patterns that include sleeping, resting and activity patterns, and user-profiled lifestyle traits that include smoking, drug use, dietary habits, body mass index and morbidities, to display to the user the prescribed lifestyle goal achieved, morbidities reduced and prognosis improved, either on the display of the user device or via device or via an active server webpage accessed through a computer connected to the Internet.

2. The method of claim 1, wherein the sensor data analysis module implements a vector filtering algorithm that uses a reference human stride motion pattern to automatically analyze confounding patterns of acceleration in X, Y and Z axes by using:
   a) a perpendicular acceleration filter,
   b) a gravity acceleration filter,
   c) a reverse acceleration filter,
   d) an orientation filter, and,
   e) an anti-aliasing filter,
for filtering longitudinal acceleration data that does not confer with the said reference pattern of human stride stored in the said sensor data analysis module, such confounding patterns of acceleration result from motions that include alternate reverse velocity in a conventional treadmill walk, or a non-human stride motion such as high speed steady velocity of a vehicle ride or bike ride, or sporadic movements of the user's hand such as for making or receiving a voice call.

3. The method of claim 1, wherein the sensor data analysis module implements a sub-module that uses a manual or automatic override algorithm when the user device incorporates a radiofrequency (RF) transponder module that detects RF signals from a synchronized RF transducer-equipped exercise equipment for allowing velocity metrics of exercise equipment based acceleration to take precedence over the user device based accelerometer.

4. The method of claim 1, wherein the Rx Zero therapeutic dose of physical activity for a completely sedentary but ambulatory patient on low calorie diet is not less than 20,000 steps per week for first four weeks, not less than 40,000 steps per week for next four weeks and 50,000 to 70,000 steps permanently thereafter, or not less than 500 MET (metabolic equivalents of task)-minutes per week for the first four weeks, not less than 1,000 MET-minutes for the next four weeks and 1,200 to 1800 MET-minutes permanently thereafter.

5. The method of claim 1, wherein lifestyle goal of the Rx Zero includes a high fiber low calorie diet that is not less than 10 calories per pound of body weight and not more than 15 calories per pound of body weight, and includes diet with fruits, vegetables, nuts and legumes, whole grains and low-fat dairy products, and no intake of sweetened beverages, processed foods and red meat.

6. The method of claim 1, wherein the rewards for achieving the goals include:
   a) to individual device user, monitory benefits such as reduction in health insurance premium corresponding to levels lifestyle change achieved, and non-monetary rewards such as improved health, reduced morbidity and mortality risk, improved treatment prognosis, better patient-caregiver interaction, motivational messages and promotional offers;
   b) to community, improved health status of population resulting in healthcare cost savings;
   c) to caregiver and policy makers, a tool that disseminates and implements primary health care and prevention at all levels of healthcare; and;
   d) to payer or insurer, decline in loss ratio on account of reduced claims.

7. The method of claim 1, wherein Rx Zero is a completely non-pharmaceutical lifestyle behavior modifying intervention, which avoids, minimizes or eliminates the prescription of pharmaceutical agents in management of chronic morbidities, and which is prescribed as initial and primary prescription limiting use of prescription drugs only to supplement the Rx Zero treatment until such time the prescription drugs are necessary in treatment of life style related chronic diseases such as hypertension, hyperlipidemia, endothelial dysfunction, metabolic syndrome, obesity, coronary artery disease, stroke, diabetes, or certain cancers such as breast cancer, prostate cancer, colorectal cancer and pancreatic cancer.

8. The method of claim 1, wherein the prescribing, administering, measuring, quantifying, monitoring, motivating and implementing a lifestyle behavior modification approach is deployed to meet specialized lifestyle needs of women pre, post and during pregnancy for improving prognosis.

* * * * *